(12) United States Patent
Yatsuo et al.

(10) Patent No.: US 7,653,426 B2
(45) Date of Patent: Jan. 26, 2010

(54) ENDOSCOPIC IMAGE PICKUP METHOD AND MAGNETIC RESONANCE IMAGING DEVICE USING THE SAME

(75) Inventors: Takeshi Yatsuo, Chiba (JP); Hisako Nagao, Chiba (JP); Kenji Sakakibara, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 420 days.

(21) Appl. No.: 10/483,444

(22) PCT Filed: Jul. 12, 2002

(86) PCT No.: PCT/JP02/07105

§ 371 (c)(1),
(2), (4) Date: Sep. 20, 2004

(87) PCT Pub. No.: WO03/005902

PCT Pub. Date: Jan. 23, 2003

(65) Prior Publication Data
US 2005/0033164 A1    Feb. 10, 2005

(30) Foreign Application Priority Data
Jul. 12, 2001    (JP) .............................. 2001-212157

(51) Int. Cl.
*A61B 5/05* (2006.01)
(52) U.S. Cl. ...................... 600/423; 600/420; 600/424; 600/410; 604/21; 604/93.01
(58) Field of Classification Search ......... 600/407–480; 606/130; 604/21, 93.01
See application file for complete search history.

(56) References Cited

U.S. PATENT DOCUMENTS
5,271,400 A    12/1993   Dumoulin et al.
(Continued)

FOREIGN PATENT DOCUMENTS
JP    06014905    1/1994
(Continued)

OTHER PUBLICATIONS
GC McKinnon, JF Debatin, DA Leung, S Wildermuth, DJ Holtz, GK von Schulthess. Towards active guidewire visualization in interventional magnetic resonance imaging. Chapman & Hall: Mar. 1996. Magnetic Resonance Materials in Physics, Biology and Medicine 4(1): pp. 13-18.
(Continued)

*Primary Examiner*—Brian Casler
*Assistant Examiner*—Amanda Lauritzen
(74) *Attorney, Agent, or Firm*—Cooper & Dunham, LLP

(57) ABSTRACT

An endoscope-like image taking method includes providing at least one peculiar index, which can be discriminated from other portions on an MR image, at the tip of a catheter, previously inserting a metal guide wire for guiding the catheter into a body cavity of a patient inserting the catheter into the body cavity along the guide wire, executing an MR imaging sequence of a plurality of sliced images intersecting the guide wire, reconstructing three-dimensional image data based upon the nuclear magnetic resonance signals, which are received by the guide wire, and determining the tip position and the inserting direction of the catheter by detecting the peculiar index provided at the tip of the catheter based upon the three-dimensional image data, and reconstructing the center projected image using the three-dimensional image data and setting the tip position and the inserting direction of the catheter as a view point and a line-of-sight direction and displaying the center projected image on a display means.

35 Claims, 8 Drawing Sheets

U.S. PATENT DOCUMENTS

| | | |
|---|---|---|
| 5,694,530 A | 12/1997 | Goto |
| 5,792,055 A | 8/1998 | McKinnon |
| 5,883,933 A | 3/1999 | Goto et al. |
| 5,928,145 A | 7/1999 | Ocali et al. ............... 600/410 |
| 6,026,316 A * | 2/2000 | Kucharczyk et al. ........ 600/420 |
| 6,061,587 A * | 5/2000 | Kucharczyk et al. ........ 600/411 |
| 6,171,240 B1 | 1/2001 | Young et al. |
| 6,272,370 B1 * | 8/2001 | Gillies et al. ............... 600/411 |
| 6,484,049 B1 * | 11/2002 | Seeley et al. ............... 600/426 |
| 6,606,513 B2 * | 8/2003 | Lardo et al. ............... 600/411 |
| 6,904,305 B2 * | 6/2005 | Tsekos ..................... 600/417 |
| 7,048,716 B1 * | 5/2006 | Kucharczyk et al. ... 604/164.01 |
| 2002/0161421 A1 | 10/2002 | Lee et al. ................. 607/116 |
| 2003/0028094 A1 | 2/2003 | Kumar et al. ............. 600/410 |
| 2004/0199071 A1 * | 10/2004 | Lardo et al. ............... 600/423 |
| 2005/0171427 A1 * | 8/2005 | Nevo et al. ............... 600/424 |
| 2006/0173284 A1 | 8/2006 | Ackerman et al. ......... 600/422 |

FOREIGN PATENT DOCUMENTS

| | | |
|---|---|---|
| JP | 07255694 | 10/1995 |
| JP | 08016813 | 1/1996 |
| JP | 10043155 | 2/1998 |
| JP | 10179550 | 7/1998 |
| JP | 10314137 | 12/1998 |
| JP | 2001070248 | 3/2001 |

OTHER PUBLICATIONS

Hurst, Gregory C., et al. "Intravascular (Catheter) NMR Receiver Probe: Preliminary Design Analysis and Application to Canine Iliofemoral Imaging", *Magnetic Resonance in Medicine*, vol. 24, No. 2, pp. 343-357, Academic Press, Deluth, MN, Apr. 1, 1992.

Aug. 20, 2008 search report in connection with a counterpart European patent application No. EP 02 74 6007.

* cited by examiner

RECEIVING AMPLIFIER 106A

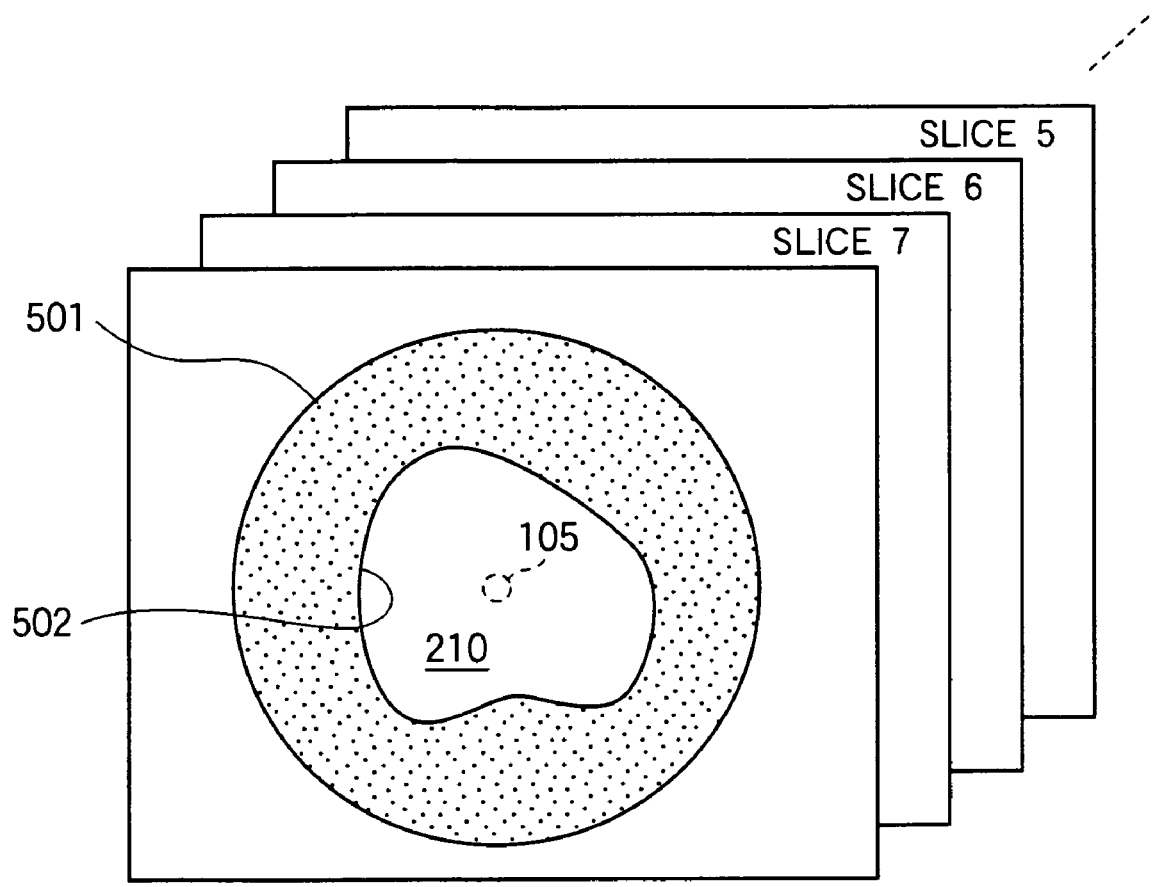

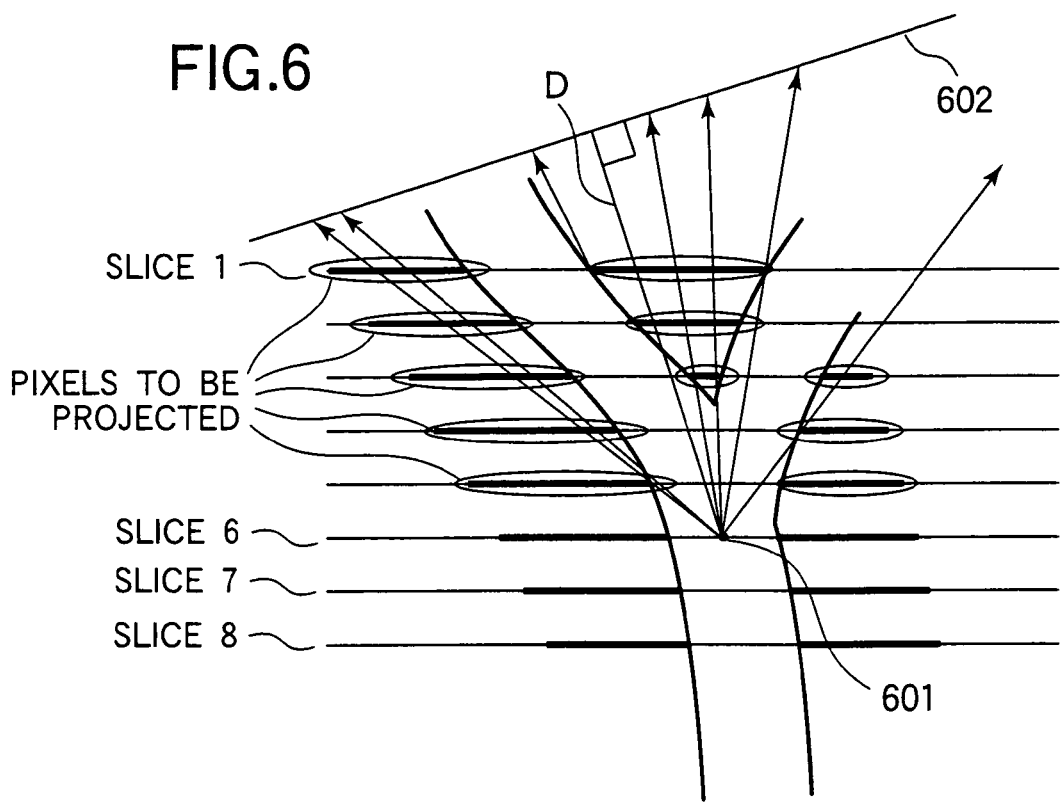
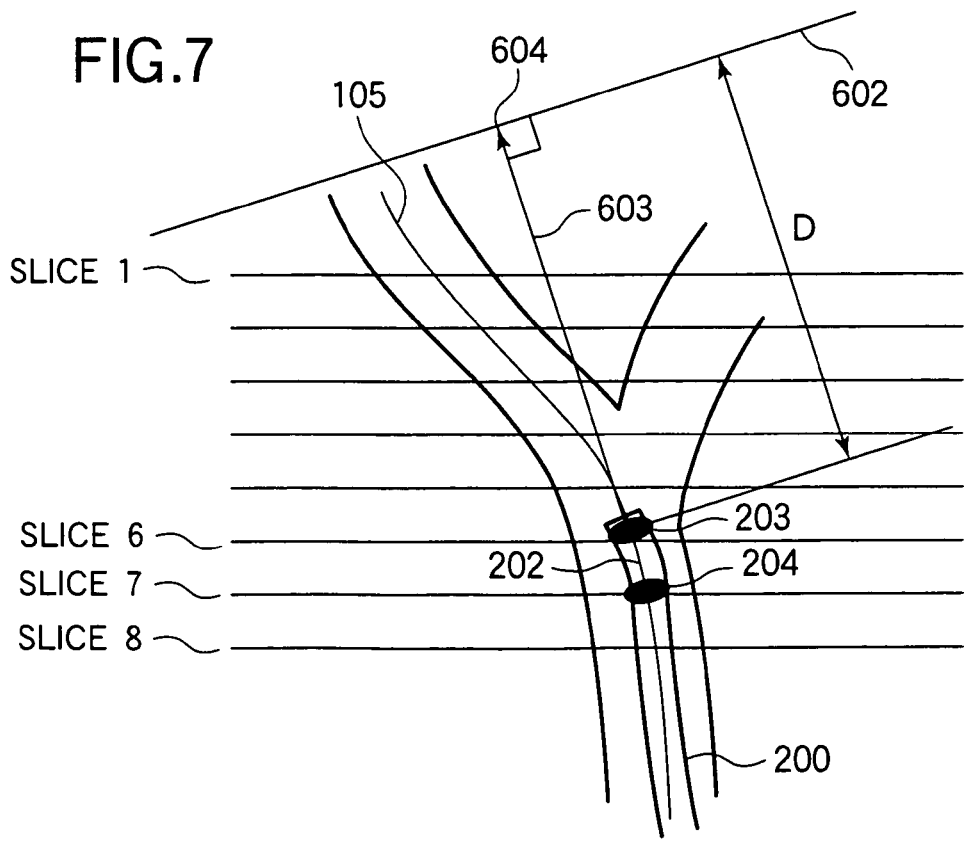

ENDOSCOPIC IMAGE PICKUP METHOD AND MAGNETIC RESONANCE IMAGING DEVICE USING THE SAME

TECHNICAL FIELD

The present invention relates to a magnetic resonance imaging apparatus (hereinafter, referred to as MRI apparatus), and more particularly, to a technology for taking and displaying an endoscope-like image of a body cavity such as a blood vessel and the like of a patient observed from a catheter inserted into the body cavity in real time.

BACKGROUND ART

An MRI apparatus is an apparatus for observing the inside of a patient by acquiring a tomogram and a frequency spectrum of a patient making use of a nuclear magnetic resonance phenomenon and includes a static magnetic field generator, a gradient magnetic field coil, a transmitting coil, and a receiving coil. The static magnetic field generator aligns the directions of the spins of nuclei (ordinarily, protons) that constitute the patient, the gradient magnetic field coil identifies the imaging slice of the patient as well as encodes position information to the nuclear magnetic resonance signals acquired from the patient, the transmitting coil generates a high frequency magnetic field having the same frequency as the resonance frequency of the protons, and the receiving coil receives the signals from the protons.

The MRI apparatus arranged as described above can selectively image any of arbitrary regions and tissues, and various imaging methods have been proposed according to patients to be imaged. For example, imaging can be executed using a two- or three-dimensional measurement. Further, in recent years, as an important field to which the MRI apparatus is applied, there has been developed a method (IV-MRI) of utilizing the MRI apparatus as the monitor of a catheter while needling or introducing the catheter into a blood vessel. In this IV-MRI, it is required to execute imaging and to display images in real time so that, for example, the catheter can be inserted to a target position without fail, and various types of a high speed imaging method such as EPI and the like have been in practical use.

In contrast, various shapes of the receiving coil have been developed and practically used according to portions to be imaged, and an RF receiving antenna, which also acts as a guide wire of the catheter, has been proposed as a receiving coil preferably used when the catheter is inserted as described above (for example, Japanese Unexamined Patent Publication No. 10-179550, PCT Japanese Translation Patent Publication No. 2000-509276, a document "Intravascular Magnetic Resonance Imaging Using a Loopless Catheter Antenna", MRM 37: 112-118 (1997), and the like). Note that since the measurable sensitivity range of the guide-wire-shaped RF receiving antenna is limited to the vicinity of the guide wire, a tomogram that can be imaged is limited to a small region (for example, several millimeters).

However, an image obtained by conventional MRI apparatuses is mainly a tomogram. Accordingly, the conventional MRI apparatuses are disadvantageous in an application for confirming the position of a catheter inserted into a body cavity such as a blood vessel having a curving portion because they cannot uniquely determine a sliced plane including the catheter. In contrast, as to a straight needle, the conventional MRI apparatuses can automatically take a tomogram on a plane including the needle or on a plane orthogonal to the needle by attaching an active or passive marker to the needle, and many conventional technologies exist. Further, as to the catheter, there is known a method of executing imaging by providing a marker, which can be identified by the MRI apparatuses, in the catheter. Since, however, a sliced plane including the catheter having a curved portion cannot be uniquely determined, it is not always easy to confirm the inserted position of the catheter.

Incidentally, the applicant has proposed a method of creating an endoscope-like image making use of three-dimensional image data acquired by an X-ray CT apparatus and an MRI apparatus as a method of displaying an image of the inside wall of a blood vessel, and the like in place of a conventional tomogram (Japanese Unexamined Patent Publications Nos. 7-210704 and 8-16813). According to the method, it is possible to convert three-dimensional tomogram data of a region including a blood vessel and the like into an image (endoscope-like image) of the inside wall of a body cavity, and the like observed from the inside by a center projecting method and to display the image, and this image is effective to diagnosis. In this case, the image may be processed according to particular shading algorithm.

However, the conventional endoscope-like image is created by a method of creating it based on three-dimensional image data that has been acquired, and further a view point and a line-of-sight direction must be input by a mouse or a track ball. Accordingly, the method cannot be applied to the IV-MRI which executes imaging and display of an image in real time.

SUMMARY

In an aspect of this disclosure, an apparatus is provided to support the insertion of a catheter by raking and displaying an endoscope-like image of the inside of a body cavity of a patient observed from the catheter in real time or semi-real time.

In another aspect of this disclosure, an endoscope-like image taking method is provided that is characterized by comprising a preparation step or providing at least one peculiar index, which can be discriminated from other portions on an MR (magnetic resonance) image, at the tip of a catheter, a first step of previously inserting a metal guide wire for guiding the catheter into a body cavity of a patient into which the catheter is inserted, a second step of inserting the catheter into the body cavity along the guide wire, a third step of executing an MR imaging (MRI) sequence of a plurality of sliced images intersecting the guide wire, a fourth step of rearranging three-dimensional image data by receiving the nuclear magnetic resonance signals, which are generated from the patient when the sequence is executed, by the guide wire and determining the tip position and the inserting direction of the catheter by detecting the peculiar index provided at the tip of the catheter based on the three-dimensional image data, and a fifth step of rearranging a center projected image using the three-dimensional image data and using the tip position and the inserting direction of the catheter as an observing point and a sight line direction and displaying the center projected image on a display means.

According to the above-mentioned imaging method, the three-dimensional image data can be obtained by sliding a body cavity to a plurality of portions in a lengthwise direction as well as the tip position and the direction of the catheter can be detected based on the three-dimensional image data. As a result, an image, which uses the tip of the catheter as a view point and is similar to an image taken by an endoscope (cruising view), can be reconstructed by a known center projected method. Accordingly, an operator can insert the catheter while observing the state of the inside wall of the body cavity, which is observed from the tip of the catheter, in real time, and this is effective to the insertion of the catheter in IV-MRI. For example, when a blood vessel is branched at a forward position, the operator can determine the branch of the blood vessel, to which a catheter is desired to guide, while observing it from a side. In particular, when the guide wire, which was blindly inserted first, is inserted into a different branch, it is easy to draw out the guide wire a little and to insert it again.

When the guide wire is composed of a receiving antenna and the intervals of the slices of the three-dimensional image data to be imaged are narrowed, an imaging time of the three-dimensional image data is increased, and thus there is a possibility that a real time imaging property may be deteriorated. Accordingly, when the intervals of the slices of the three-dimensional image data is widened, it is contemplated that detecting peculiar indexes provided with the catheter based on the three-dimensional image data is difficult.

In response thereto, another imaging method is provided in another aspect of this disclosure, wherein three-dimensional image data, which is reconstructed by executing an MR imaging sequence to a plurality of slices that intersect the guide wire, is stored. Then, the tip position and the inserting direction of the catheter can be detected by executing a measuring sequence, which measures the NMR signals of the tip of the catheter in the three-axis directions thereof, projecting the measured NMR signals in the respective axis directions and using the projections of the three axes to which the NMR (nuclear magnetic resonance) signals are projected. That is, when the tip position and the inserting direction of the catheter is detected by a three-axis projection method having a short measuring time, the real time imaging property can be maintained by increasing the frequency of detection of the tip position and the inserting direction of the catheter even if the imaging frequency of the three-dimensional image that takes a long measuring dine is reduced. That is, the imaging sequence of the three-dimensional image data, which is used as the base of the center projection, can be executed once every time the processing for rearranging a center projected image by detecting the tip position and the inserting direction of the catheter is executed once.

Further, in still another imaging method, according to another aspect of this disclosure, the number of slices can be reduced by detecting the tip position and the inserting direction of the catheter by executing beforehand the measuring sequence that measures the NMR signals of the tip of the catheter in the three-axis directions thereof, setting sliced positions forward of the detected tip position of the catheter, and executing the MR imaging sequence of a plurality of sliced images intersecting the guide wire, and thereby the measuring time of the three-dimensional image data can be reduced.

In the above-mentioned approaches, a ring-shaped marker, which is provided at the tip of the catheter coaxially with the catheter, can be used as the peculiar index. In this case, it is preferable to provide at least two markers at the tip of the catheter by displacing the positions thereof in the axial direction of the catheter. According to the above arrangement, an accuracy of detecting the direction of the catheter can be improved as compared with the case in which one marker is provided.

In another aspect of this disclosure, an MRI apparatus includes a magnetic field generation means for generating the respective magnetic fields of a static magnetic field, a gradient magnetic field, and a high frequency magnetic field that are applied to a patient, a receiving means far receiving the nuclear magnetic resonance signals generated from the patient, an image reconstruction means for rearranging the three-dimensional image data of the patient using the thus received nuclear magnetic resonance signals, a display means for displaying a reconstructed image, and a control means for controlling the magnetic field generation means, the receiving means, and the image reconstruction means, wherein at least one peculiar index, which can be discriminated from other portions on an MR image, is provided at the tip of a catheter inserted into a body cavity of the patient as well as a metal guide wire for guiding the catheter is used as the receiving means, and the image reconstruction means reconstructs three-dimensional image data using the nuclear magnetic resonance signals received by the guide wire, detects the peculiar index using the thus reconstructed three-dimensional image data, determines the tip position and the inserting direction of the catheter based on the peculiar index, and reconstructs a center projected image using the three-dimensional image data and using the tip position and the inserting direction of the catheter determined as described above as an observing point and a sight line direction and displays the center projected image on the display means.

That is, in the above-mentioned MRI apparatus, the guide wire is inserted into a body cavity, for example, a blood vessel of a patient as an RF receiving antenna, the catheter is inserted while nuclear magnetic resonance (NMR) signals being continuously acquired by the RF receiving antenna, the tip position of the catheter is detected from the acquired signals, and an image having a view paint along the direction of the catheter is reconstructed from the acquired signals and displayed. With the above operation, an image (as if observed by inserting an endoscope) can be displayed while inserting the catheter.

Moreover, although only a visible image can be displayed in an ordinary endoscope, since an image as if acquired by the endoscope can be reconstructed in the above-mentioned apparatus, it is possible to display functional information, which can be acquired only by the MRI apparatus, for example, the infarct and the blood clot in a blood vessel, and particular tissues such as plaques, fats and the like.

Further, in the above-mentioned MRI apparatus, the respective steps of measuring the nuclear magnetic resonance signals used to acquire the three-dimensional image data, determining the view point and the line-of-sight direction used in the center projection, and rearranging and displaying an endoscope-like image are executed repeatedly. Preferably, when the steps are repeated at a speed of one cycle per second, the endoscope-like image can be displayed in approximate real time.

BRIEF DESCRIPTION OF THE DRAWINGS

FIG. 5 is a view showing an example of three-dimensional image data acquired by the endoscope-like image taking method of the present invention;

FIG. 6 is a view explaining center projecting processing in the endoscope-like image taking method of the present invention;

FIG. 7 is a view explaining a method of creating a center projected image in the endoscope-like image taking method of the present invention;

BEST MODE FOR CARRYING OUT THE INVENTION

Embodiments of the present invention will be explained with reference to the figures in detail.

Figure 1:
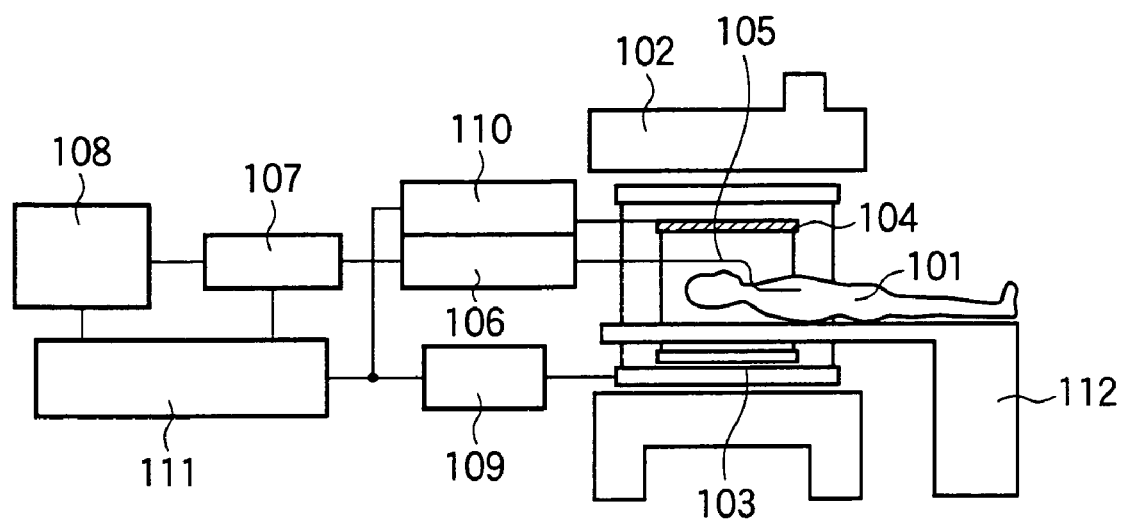
FIG. 1 shows the overall arrangement of an MRI apparatus of an embodiment to which the present invention is applied.

FIG. 1 shows the overall arrangement of an MRI apparatus to which the present invention is applied. The MRI apparatus includes a static magnetic field magnet 102, a gradient magnetic field generating coil 103, an RF irradiating coil 104, a guide wire 105 that also acts as an RF receiving antenna for detecting nuclear magnetic resonance signals generated from a patient 101, and a bed 112 for carrying the patient into a measuring space, and these components are installed in an imaging room. The static magnetic field magnet 102 generates a uniform magnetic field in the measuring space, the gradient magnetic field generating coil 103 gives a magnetic field gradient to the static magnetic field generated by the static magnetic field magnet 102, and the RF irradiating coil 104 irradiates a high frequency magnetic field to the patient placed in the measuring space.

A permanent magnet, a normally conductive electro-magnet or a superconductive electro-magnet is used as the static magnetic field magnet 102 and generates a uniform static magnetic field in a direction orthogonal to or in parallel with the body axis of the patient 101 in the measuring space in which the patient 101 is placed. The illustrated example employs an open type static magnetic field magnet 102 which is composed of a pair of the static magnetic field magnets disposed in upper and lower portions in the measuring space so as to form a static magnetic field in an up/down direction (direction orthogonal to the body axis of the patient 101) so that an IV-MRI apparatus can be operated easily.

The gradient magnetic field generating coil 103 is composed of three coils that generate gradient magnetic fields in three-axis directions orthogonal to each other, respectively and connected to a gradient magnetic field power supply 109, respectively. The RF irradiating coil 104 is connected to a transmitting circuit 110 having an oscillator, which generates a high frequency wave having the same frequency as the resonance frequency of protons, a modulator, and an amplifier.

Figure 2:
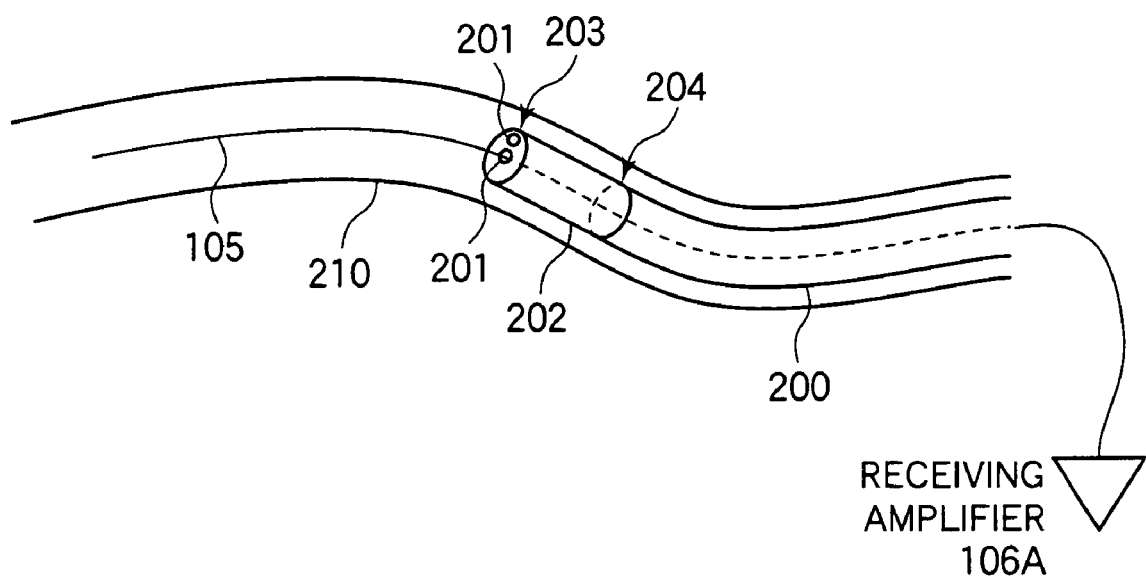
FIG. 2 is a view explaining a guide wire also acting as an RF receiving antenna according to the present invention and a state of use of a catheter guided by the guide wire.

The guide wire 105 also acting as the RF receiving antenna is connected to a receiving circuit 106 having a receiving amplifier, a phase detector, an A/D converter, and the like. The guide wire 105 is formed of a thin and flexible metal wire to achieve a function for guiding a catheter 200 which is inserted into a body cavity as well as connected to a receiving amplifier 106A at an end as shown in FIG. 2 to achieve the function of the RF receiving antenna. Further, the guide wire 105 is preferably formed of a non-magnetic metal wire so as not to disturb the distribution of a magnetic field. A loopless catheter antenna disclosed in, for example, "Intravascular Magnetic Resonance Imaging Using a Loopless Catheter Antenna" (MRM37: 112-118 (1997)" may be used as the guide wire 105 also acting as the RF receiving antenna.

Note that this embodiment may have an overall body or partial body RF receiving coil, which is provided with an ordinary MRI apparatus, in addition to the guide wire 105 also acting as the RF receiving antenna.

The gradient magnetic field power supply 109, the transmitting circuit 110, and the receiving circuit 106 are installed outside of the imaging room and controlled by a computer 111 installed outside of the imaging room likewise. The operations of the gradient magnetic field power supply 109, the transmitting circuit 110, and the receiving circuit 106 are controlled through a sequencer 107 based on an imaging sequence set in the computer 111. Further, captures the nuclear magnetic resonance signals received by the transmitting circuit 110 and reconstructs an image by executing arithmetic operations such as an interpolating calculation, Fourier transform, and the like. The computer 111 includes a console through which processing conditions, and the like are input and set, a storage device for storing programs, data being processed, data having been processed, and the like, a display unit 108 for displaying a reconstructed image, and the like.

Further, the computer 111 creates three-dimensional image data using the nuclear magnetic resonance signals received by the transmitting circuit 110 as well as determines a view point and a line-of-sight direction based on a peculiar index included in the three-dimensional image data as described later, subjects the three-dimensional image data to center projecting processing, creates an endoscope-like image, and displays the image on the display unit 108.

On the other hand, the catheter 200 has a hole 201 extending in an axis direction as shown in FIG. 2 so that the guide wire 105 is passed therethrough. Note that, although not shown, the catheter 200 ordinarily has a plurality of holes extending in the axial direction so that a device for collecting a tissue and a balloon are passed therethrough. In particular, the catheter 200 of this embodiment has two ring-shaped markers 203 and 204 provided at the tip 202 thereof. These markers 203 and 204 are formed of a material that can be identified from the images of a tissue and the like other than the markers on an MR image. For example, a material, which has high luminance in response to nuclear magnetic resonance (NMR) signals, may be buried in the catheter as a positive marker. On the contrary, a material, which causes a signal defect in response to the NMR signals, may be buried in the catheter as a negative marker. Many methods are known as a method of burying the markers 203 and 204 in the catheter 200, and any of the methods may be employed. For example, there are employed a method of burying paramagnetic metal powder as the maker, a method of using a contrast agent in the catheter 200 as the marker, a method of drawing out a conductor to the outside, supplying a current to the conductor, and making the conductor visible by a signal defect caused by the disturbance of a magnetic field due to the current, and the like. In short, it is sufficient to form the markers 203 and 204 of a material and the like which can be identified from the images of other tissue, and the like on the MR image. As described above, a view point and a line-of-sight direction for creating an endoscope-like image, which will be described later, are determined based on the position and the direction of the markers 203 and 204 that can be identified on the MR image.

Figure 3:
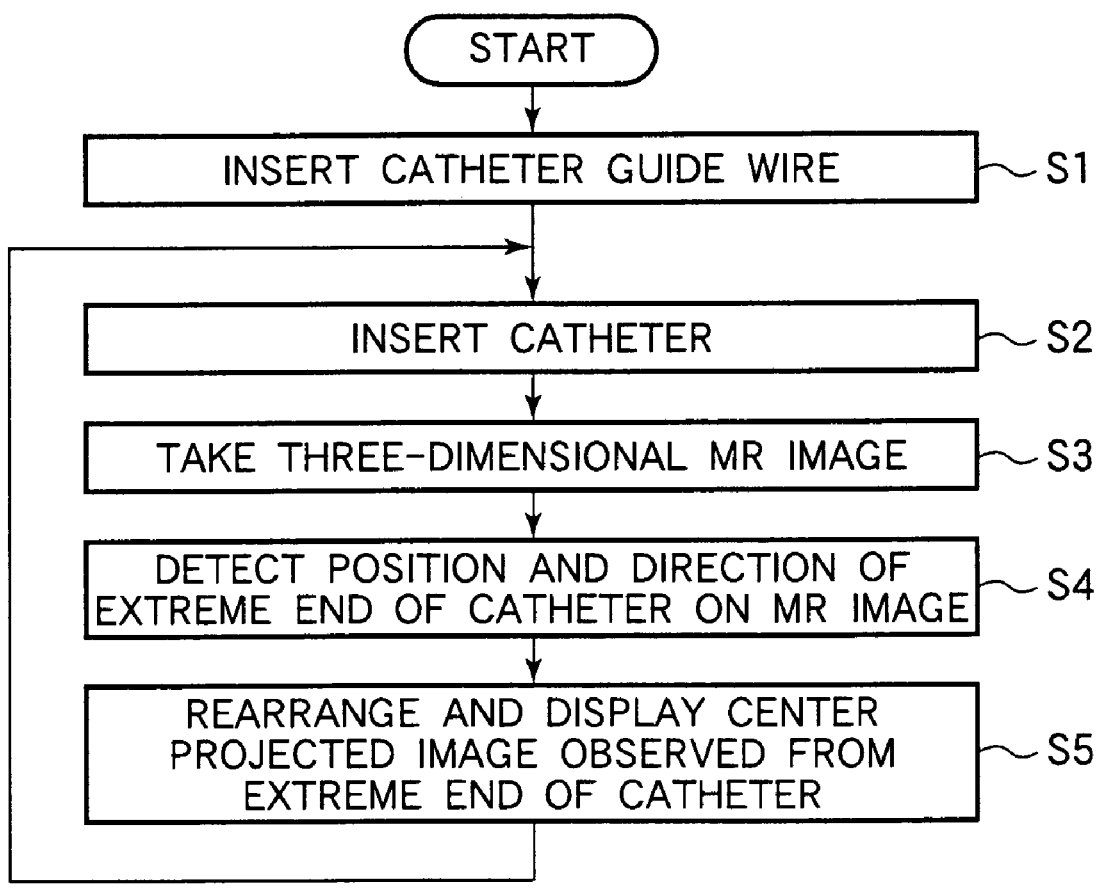
FIG. 3 is a flowchart showing a procedure of an embodiment according to an endoscope-like image taking method of the present invention.

The detailed arrangement of the MRI apparatus of the embodiment will be explained below together with its operation. FIG. 3 shows an example of a continuous imaging procedure when the catheter is inserted. First, the patient 101 is laid on the bed 112, inserted into the static magnetic field, and positioned at the center of the static magnetic field in FIG. 1. Next, the guide wire 105 also acting as the RF receiving antenna is blindly inserted into a blood vessel 210 of the patient 101 shown in FIG. 2 that is a subject to be diagnosed or treated (step S1). The method of inserting the guide wire 105 is the same as a conventional guide wire inserting method, and the guide wire is inserted to a position near to the portion to be inspected of the patient 101. At this time, when the guide wire 105 can be identified by NMR signals, it may be inserted while being imaged. Thereafter, the catheter 200 is inserted along the guide wire 105 as shown in FIG. 2 (step S2).

When the tip 202 of the catheter 200 approximately reaches a portion that is desired to be observed, an MR image starts to be taken to create an endoscope-like image (step S3). An imaging method (imaging sequence) is not particularly limited as long as it can collect three-dimensional image data in a short time. For example, single shot EPI and multi shot EPI can be applied. Further, the three-dimensional image data may be created by cumulating a plurality of two-dimensional tomogram data or may be measured by a three-dimensional imaging sequence.

Figure 4:
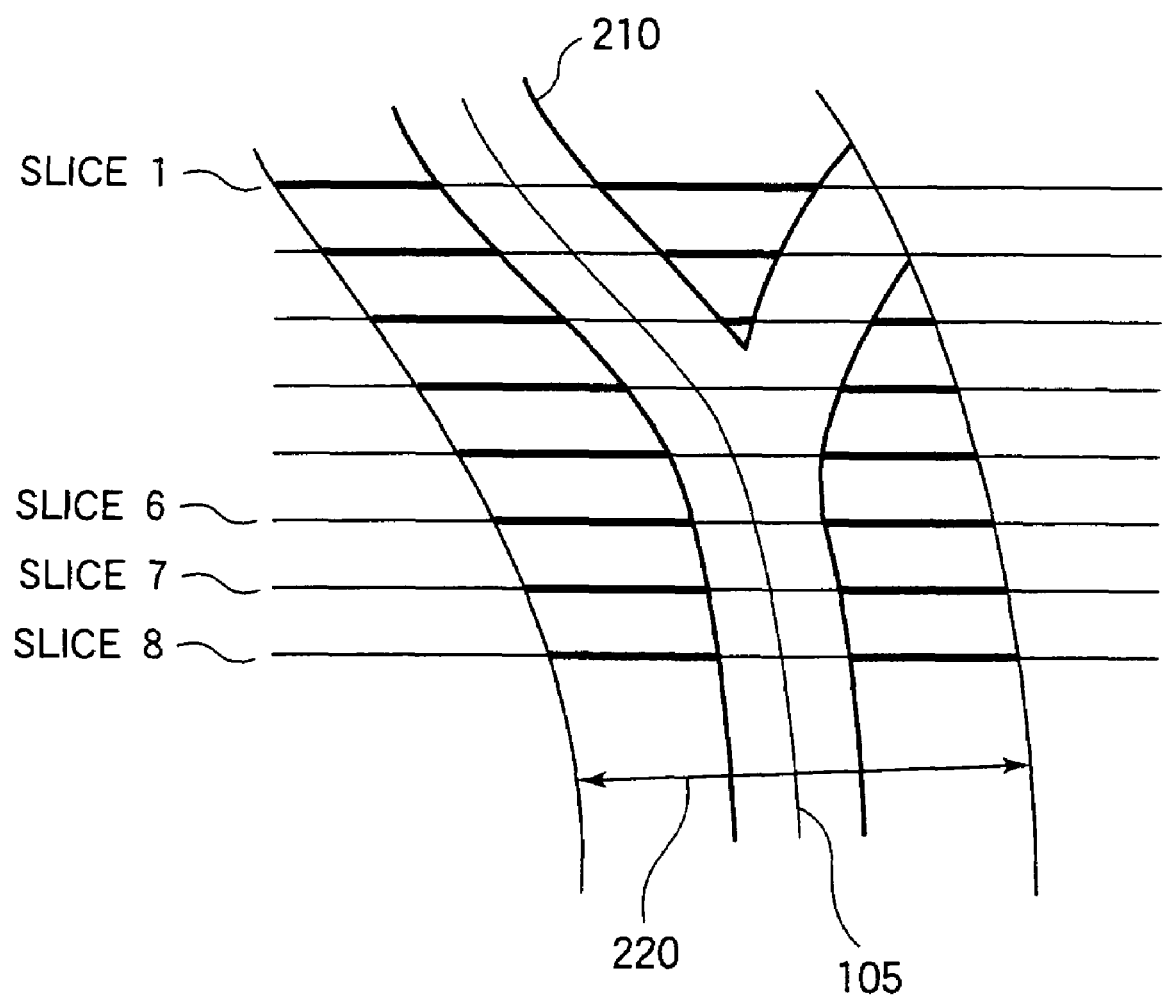
FIG. 4 is a view showing an example of three-dimensional image data acquired by the endoscope-like image taking method of the present invention.

FIGS. 4 and 5 show schematic views of the three-dimensional image data acquired by the imaging executed at step S3. In the illustrated example, imaged slices (for example, slices 1 to 8) are selected approximately vertically with respect to the blood vessel 210 into which the catheter 200 is inserted, and a plurality (for example, eight sheets) of slice image data is acquired by sequentially repeating the imaging while changing the slices. Since the effective sensitivity range of the guide wire 105 is narrow, only the NMR signals of a narrow region 220 along the guide wire 105, that is, along the blood vessel 210 are acquired. For example, the portion surrounded by a circle 501 in FIG. 5 shows the sensitivity range of the guide wire 105. Ordinarily, since the NMR signals cannot be measured in the blood vessel 210 due to a blood flow, a voided image is formed to a blood vessel wall 502, and a black image is formed to the region outside of the blood vessel 210. Further, since the guide wire 105 is formed of a material which causes a signal defect in the NMR signals as described above, a white image is formed to the guide wire 105.

Next, the computer 111 reconstructs the endoscope-like image by executing the center projecting processing using the acquired three-dimensional image data (steps S4 and S5). In the center projecting processing, first, a projection plane 602 is set at a position apart from a predetermined view point 601 a predetermined distance (focal distance) D in a predetermined direction (line-of-sight direction) as shown in FIG. 6 so that the projection plane 602 is orthogonal to or intersects the line-of-sight direction. Next, processing for projecting the pixel data of the respective slices 1 to 8 onto the projection plane 602 is executed, that is, processing for converting the coordinates of the pixels of the slices 1 to 8 into the coordinate of the projection plane 602 is executed. Specifically, the processing can be executed using the technologies disclosed in Japanese Unexamined Patent Publications Nos. 7-120704 and 8-16813. That is, when the angles between the planes of the slices 1 to 8 and the projection plane 602 and the distances between the view point 601 and the pixels of the slices 1 to 8 are determined, the coordinates of the pixels of the slices 1 to 8 can be converted into the coordinate of the projection plane. Then, the angles between the slice plane and the projection plane 602 and the distances between the view point 601 and the pixels of the slice plane can be determined from the coordinate of the view point, the line-of-sight direction, and the focal distance D.

To execute the center projecting processing, the computer 111 determines the coordinate and the line-of-sight direction of the view point 601 using the markers (peculiar indexes) included in the acquired three-dimensional image data (step S4). When the tip of the catheter 200 including the markers 203 and 204 reaches sliced planes at the time the MR image is taken at step S3, the image data of the slices 6 and 7 of the three-dimensional image data having been taken includes the images of the markers 203 and 204 as shown in FIG. 7. Accordingly, the tip position of the catheter 200 can be detected from, for example, the position of the marker 203. Further, the inserting direction of the catheter 200 can be detected from a straight line connecting the marker 203 to the maker 204.

That is, the two markers 203 and 204 are provided at the tip of the catheter 200 and at a position located somewhat backward of the tip. Then, for example, the position of the marker 203 provided at the tip is used as the view point. Further, the straight line connecting the two markers 203 and 204 is used as a line-of-sight vector 603, and the point, which is located on a line extending from the line-of-sight vector 603 and has the predetermined distance D from the marker 203 acting as the view point is used as the point of origin 604 of the projection plane 602. The plane, which passes through the point of origin 604 and orthogonal to the line-of-sight vector 603 to the line-of-sight vector 603, is determined as the projection plane 602.

A longer focal distance D results in a narrower viewing angle, from which an image as if it was observed through a telescopic lens can be acquired. In contrast, a shorter focal distance D results in a wider viewing angle, from which an image as if it was observed through a wide-angle lens can be acquired. The focal distance D may be previously set according to the thickness of a blood vessel to be observed or an object of diagnosis or may be set through the console of the computer 111 in each case.

Note that the computer 111 differently recognizes the markers 203 and 204 from the three-dimensional image depending on whether the markers 203 and 204 are positive markers or negative markers. When, for example, the markers 203 and 204 are negative markers and the region of the pixels having the lowest signal value exists in the periphery of the pixels having the lowest signal value (pixels corresponding to the guide wire 105 in this example) among the pixels in the blood vessel wall 502 in the sliced image data in FIG. 5, it is determined that the marker 203 exists in the region. Then, the center coordinate of the marker 203 is set as the view point 601. In addition to the above, a method using pattern recognition, and the like can be employed.

When the view point and the line-of-sight direction are determined as described above, center projection is executed from the view point 601 to the projection plane 602 in the figure that is defined at step S4 (step 5). With this operation, the pixel values of the respective slices 1 to 8 are projected onto the projection plane 602 in a radial pattern about the view point 601. This processing is sequentially executed from the slices located farther from the view point 601, and when the pixel value of a next slice overlaps the pixel value having been projected, the projected pixel value is overwritten with the pixel value nearer to the view point. An image (endoscope-like image), which is observed from the view point 601, is formed on the projection plane 602 by sequentially overwriting the projected pixel values with the pixel value of the slice nearer to the view point 601 as described above.

Shading algorithm, which is known as a depth method and a volume rendering method, may be applied to the thus acquired endoscope-like image, thereby the light and shade portions of the endoscope-like image can be more easily discriminated.

Figure 8:
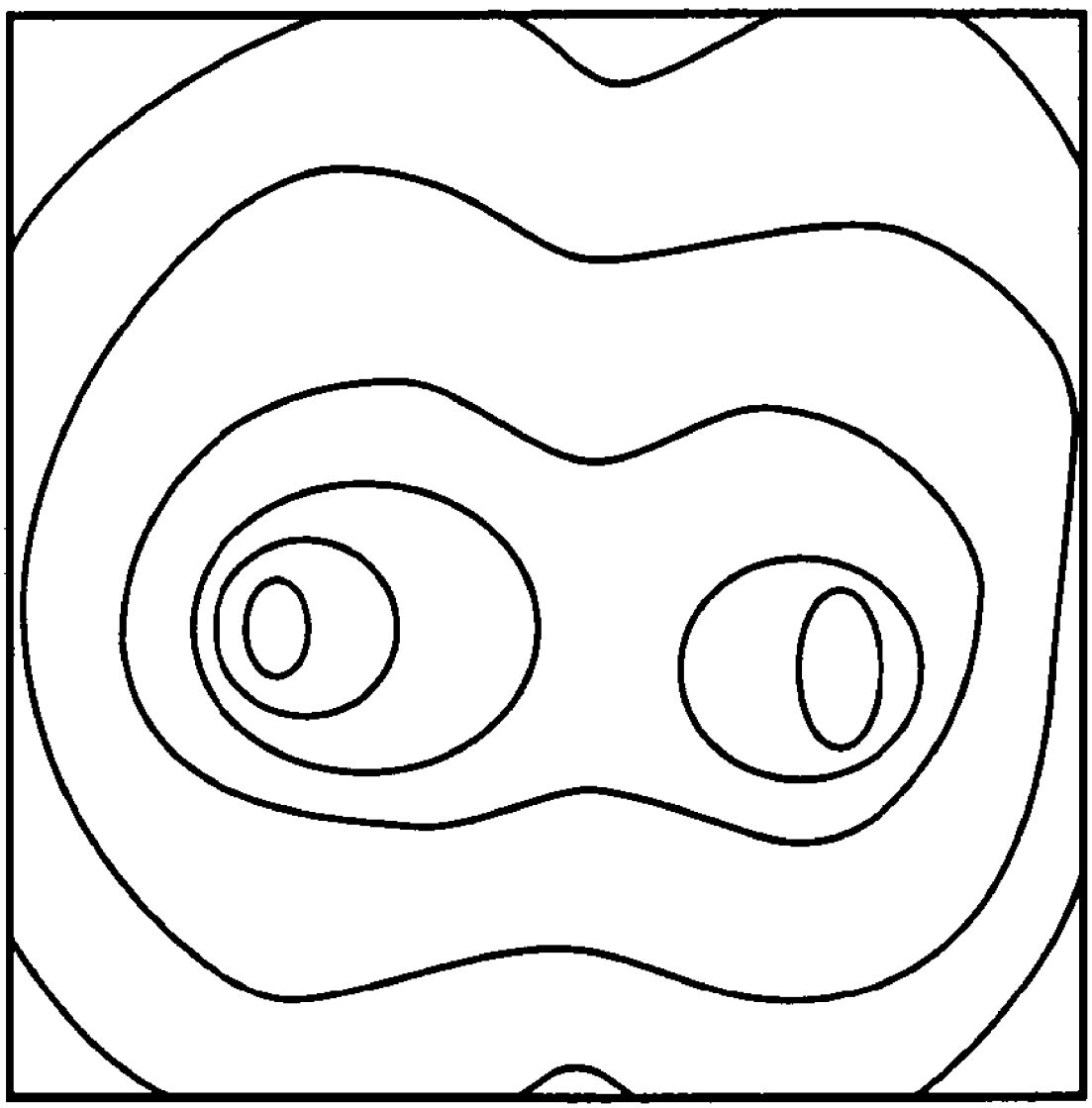
FIG. 8 is a view schematically showing an endoscope-like image acquired by the center projecting processing.

FIG. 8 schematically shows an endoscope-like image acquired as described above. Since the image is displayed on the display unit 108, an operator can further move the catheter forward while observing the image. When steps S2 to S5 are repeated in time with the forward movement of the catheter, a new endoscope-like image having a different view point and line-of-sight direction is displayed.

Since the endoscope-like image is an image of the inside of a blood vessel when it is observed from the tip of the catheter, the branching state and the like of the blood vessel can be easily found in relation to the catheter. Accordingly, it is possible to determine a direction in which the guide wire is to be inserted while observing the branch of the blood vessel. Further, since the endoscope-like image is created using the NMR signals received by the guide wire 105 also acting as the RF receiving antenna, an image, which has a high S/N ratio only in the narrow portion in the periphery of the blood vessel and the like into which the guide wire is inserted, can be acquired. Accordingly, it is possible to observe a blood vessel wall and the periphery of a portion that is desired to be observed in conjunction with the insertion of the catheter.

Further, it is preferable to employ a high speed imaging method by which three-dimensional image data can be acquired on the order of 100 milliseconds in a sequence for imaging the three-dimensional image data using the NMR signals received by the guide wire. According to this method, the cycle from step S2 to step S5 can be repeated at a speed of, for example, one cycle per second, thereby an image, which varies in conjunction with the movement of the catheter, can be displayed approximately in real time. The operator executes observation while the cycle is repeated and can effectively execute IV-MRI such as a biopsy using a surgical tool through the catheter when necessary.

Although the embodiment of the present invention has been described above, the present invention is by no means limited thereto and may be variously modified. For example, the embodiment shown in FIG. 3 explains the case that the imaging of the three-dimensional image data and the reconstruction of the image, and the reconstruction and the display of the endoscope-like image are repeated in real time. However, the three-dimensional image data need not be necessarily acquired each time the reconstruction and the display of the endoscope-like image are repeated. For example, the two-dimensional image may be acquired every time the reconstruction and the display of the endoscope-like image are repeated a plurality of times.

Figure 9:
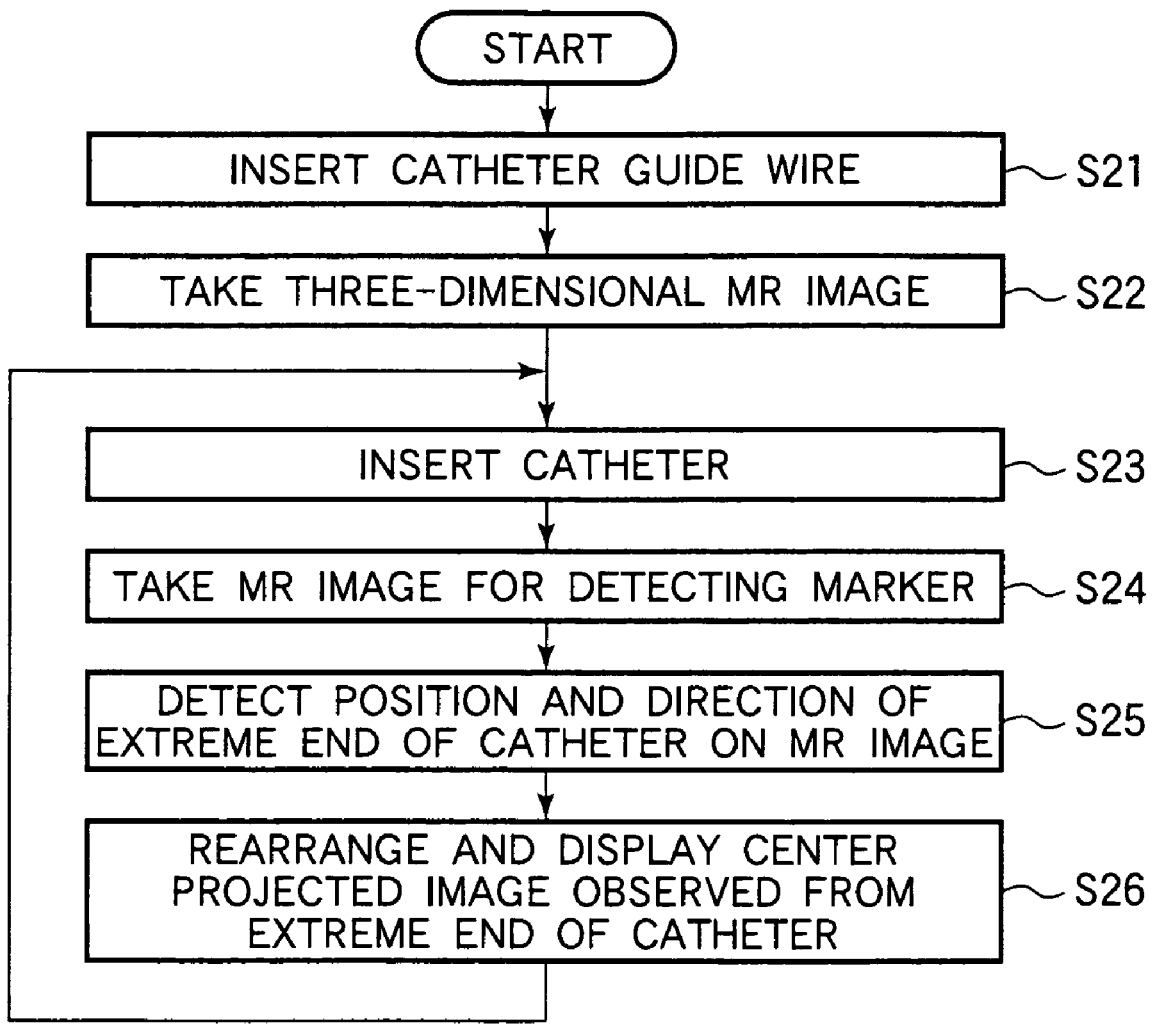
FIG. 9 is a flowchart showing a procedure of another embodiment of the endoscope-like image taking method according to the present invention.

Further, three-dimensional image data may be acquired prior to the insertion of a catheter 200, and the reconstruction and the display of an endoscope-like image may be repeated using the three-dimensional image data as shown in FIG. 9. Also in this embodiment, first, peculiar indexes of two markers 203 and 204, which can be discriminated from other portions on an MR image, are provided at the tip 202 of the catheter 200 as a preliminary step executed prior to the execution of imaging. When the imaging starts, a non-magnetic metal guide wire 105, which guides the catheter 200 into a blood vessel 210 of a patient 101 into which the catheter 200 is inserted, is previously inserted into the blood vessel (step S21). The guide wire 105 also acts as an RF receiving coil similarly to the guide wire 105 used in the embodiment described above. Then, before the catheter 200 is inserted, MR imaging is executed to acquire the three-dimensional image data covering a relatively large region including the guide wire 105 and a target portion, and the three-dimensional image data that has been reconstructed is stored in a storage device of the computer 111 (step S22). Next, the catheter 200 is moved forward along the guide wire 105 (step S23), and when it approaches the target portion, marker detecting MR imaging is executed to detect the positions of the markers 203 and 204 provided at the tip 202 of the catheter 200 (step S24). The MR imaging sequence may be a sequence similar to the imaging sequence executed at step S22. In this case, the MR imaging at step S24 is executed to image a relatively narrow region because it is required to detect only the positions of the markers 203 and 204. That is, the slices, which are approximately orthogonal to the blood vessel 210, are imaged in FIG. 4. In this embodiment, however, since the position of the blood vessel 210 can be found from the three-dimensional image data previously acquired at step S22, the MR imaging at step S24 may be executed to sliced planes which are sections including the blood vessel 210. With this operation, the number of the slices can be reduced.

Further, in place of the above method, the MR imaging method at step S24 may be executed such that a measurement sequence, which measures the NMR signals of the tip 202 of the catheter 200 in the three-axis directions thereof is executed, the thus measured NMR signals are projected in the respective axis directions, and the tip 202 of the catheter 200 is detected based on the projections of the three axes to which the NMR signals are projected. The NMR signals at this time are received by an ordinary RF receiving coil disposed outside of the patient 101.

The position (view point) of the marker 203 on the extreme end side of the tip 202 of the two markers 203 and 204 and the line connecting the two markers 203 and 204 (line-of-sight direction) can be detected from the thus acquired image or NMR signals (step S25).

Next, the position of the marker 203 detected at step S25 is determined as the view point, the line connecting the two markers 203 and 204 is determined as the line-of-sight direction, center projecting processing is executed using the three-dimensional image data acquired at step S22, and an endoscope-like image is reconstructed (step S26). That is, as explained in FIG. 6, an image viewed from the view point is created by executing center projecting processing to the projection plane 602 having the predetermined focal distance D. As described above, an endoscope-like image, in which the image in the blood vessel varies according to the forward movement of the catheter 200, is displayed similarly to an endoscope by repeating the processing from steps S23 to S26 while moving the catheter 200.

According to the embodiment of FIG. 9, since the marker detecting MR imaging can be executed at step S24 in a relatively narrow region or to a smaller number of slices, an imaging time can be reduced, it can be executed in a time shorter than that of the MR imaging executed at step S3 in the embodiment of FIG. 3. Thus, according to this embodiment, a real time imaging property can be more improved. In this embodiment, however, since the MR imaging for acquiring the three-dimensional image data and the MR imaging for detecting the markers of the catheter are executed at different timing, when the shape of the blood vessel is varied by the insertion of the catheter, or when it is desired to observe the variation of the shape of the blood vessel, it is preferable to execute the embodiment of FIG. 3.

Figure 10:
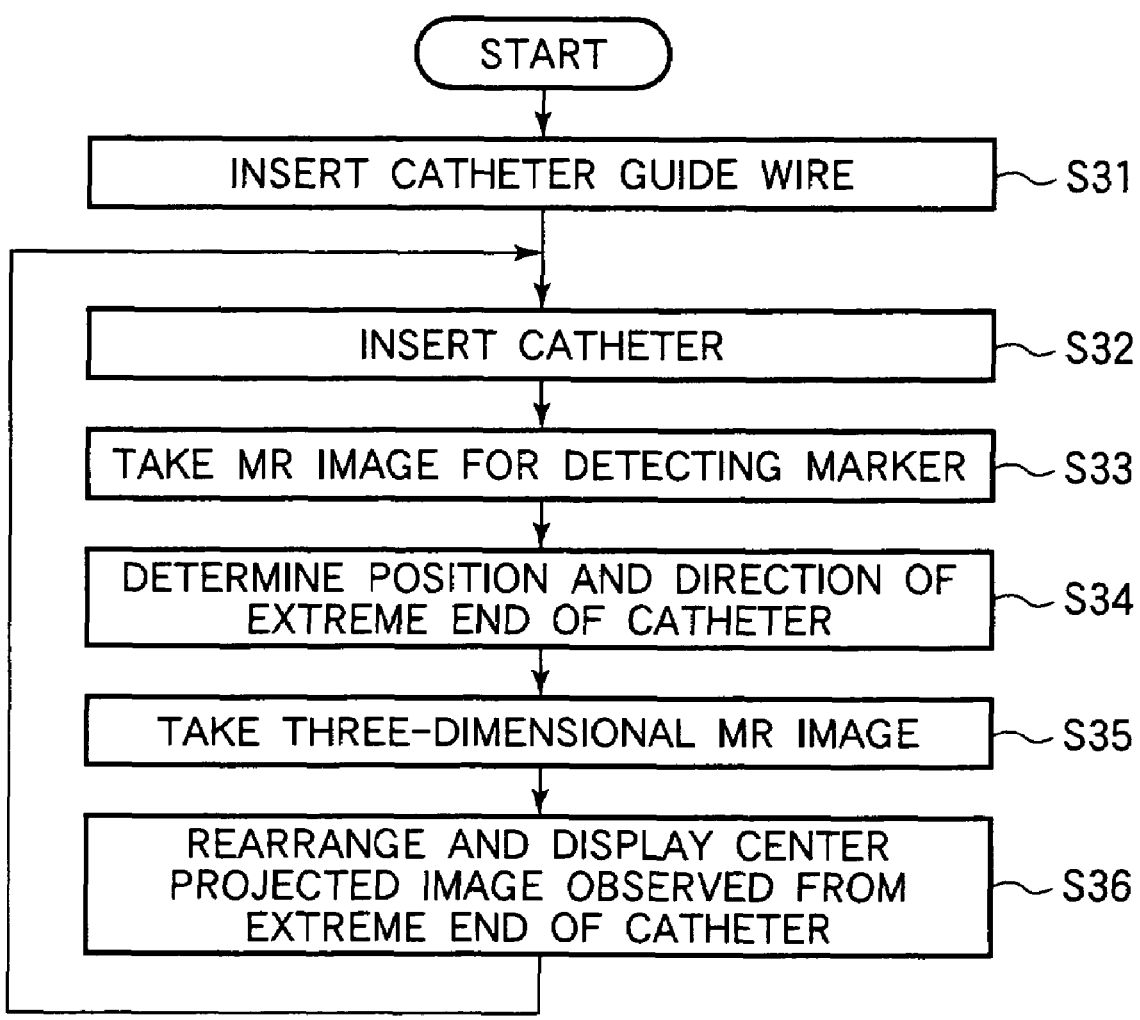
FIG. 10 is a flowchart showing a procedure of still another embodiment of the endoscope-like image taking method according to the present invention.

FIG. 10 shows a flowchart of other embodiment according to the imaging method of an endoscope-like image of the present invention. Also in this embodiment, peculiar indexes of two markers 203 and 204, which can be discriminated from other portions on an MR image, are provided at the tip 202 of a catheter 200 as a preliminary step prior to the execution of imaging. When the imaging starts, a non-magnetic metal guide wire 105, which guides the catheter 200 into a blood vessel as an example of a body cavity of a patient 101 into which the catheter 200 is inserted, is previously inserted to a target portion (step S21). Although the guide wire 105 is blindly inserted basically, it may be inserted while being monitored through MR imaging executed as necessary. Then, the catheter 200 is inserted into the blood vessel along the guide wire 105 (step S32).

Next, an MR imaging sequence is executed to the tip 202 of the catheter 200 to detect the tip 202 (step S33). The MR imaging sequence is a sequence called a projection method by which each of three axes is measured and the signals of the three axes are projected. That is, the thicknesses and the positions of slices are set at intervals in the lengthwise direction of the catheter 200 such that each of the slices contains the markers 203 and 204 acting as peculiar images that can be discriminated from other portions in an MR image, and the NMR signals of the three orthogonal axes are measured. Here, three-axis directions are, for example, the directions in which a lying patient 101 has sliced planes of a horizontal section (COR), a vertically longitudinal section (SAG), and a vertically lateral section (TRS).

When the signals in the three-axis directions are measured at step S33, the NMR signals generated from the patient 101 is received by a ordinary RF receiving coil disposed outside of the patient 101, and the respective received signals are projected in the respective axis directions. Next, the positions of the geometrical markers 203 and 204 are detected based on the projections of three axes to which NMR signals are projected. Then, the tip position and the direction of the catheter 200 are determined using the marker 203 as a view point and the direction of the straight line connecting the marker 203 to the maker 204 as the direction of the catheter 200, that is, a line-of-sight direction (step S34). Note that unless the forward moving direction of the catheter 200 is not changed, it can be traced by the projections in two axis directions and it is not necessary to measure the projections of the three axes, and thus a measuring time can be shortened by switching a measuring sequence. Note that the geometrical position of the tip 202 of the catheter 200 may be detected by a method of taking two-dimensional images or three-dimensional images in the three-axis directions thereof.

Next, an MR imaging sequence of a plurality of sliced images, which are approximately orthogonal to the guide wire 105, is executed (step S35). The NMR signals, which are generated from the patient 101 when the above sequence is executed, are received by the guide wire 105, and three-dimensional image data is reconstructed by the computer 111. Then, a center projected image is reconstructed using the three-dimensional image data and setting the tip position and the inserting direction of the catheter 200 as the view point and the line-of-sight direction, and the reconstructed center projected image is display on a display means (step S6).

As described above, according to the embodiment of FIG. 10, since the tip position and the direction of the catheter 200 are detected and the three-dimensional image data is acquired based on them using the guide wire as the RF receiving antenna, the imaging range of a three-dimensional image can be set forward of the tip position of the catheter 200. Further, since the geometrical positions of the markers 203 and 204 are detected using the projection method, a time for detecting the positions can be shortened. As a result, the number of slices of the three-dimensional image can be reduced. That is, according to the embodiments of FIGS. 3 and 9, since the three-dimensional image data is acquired before the position of the catheter 200 is detected, sliced plane must be set in a certain range in front of and behind of a presumed position of the catheter. Accordingly, image data behind the catheter, which is not necessary to the center projection, is acquired, and an imaging time is increased thereby.

As described above, according to the respective embodiments of the present invention, when the MRI imaging is executed while inserting the catheter into a blood vessel and the like of a patient, the tip position and the direction of the catheter are detected from the signals acquired in real time, and an image, which is subjected to the center projecting processing using the tip position as the view point, is reconstructed. Thus, a real time image as if it was observed by inserting an endoscope can be displayed while inserting the catheter. As a result, the present invention is effective in a catheter inserting operation in the IV-MRI. For example, when a blood vessel is branched at a forward position, the branch of the blood vessel to which the catheter is desired to guide can be determined while observing an image.

Further, although the catheter is provided with the two markers and the direction (line-of-sight direction) of the catheter is determined by the markers, it is sufficient to provide at least one marker at the tip thereof. When the catheter is provided with one marker and the MR imaging is repeated while moving the catheter forward, the line-of-sight direction can be detected by determining the positional variation of the marker by an arithmetic operation each time the MR imaging is repeated.

Further, the case that the two-dimensional data is cumulated as the three-dimensional data has been described in the embodiments described above. However, the present invention is by no means limited thereto, and the three-dimensional data may be acquired by a three-dimensional measurement executed at step S3 or at steps S22 and S24.

Further, the case that the morphological image of a blood vessel wall is simply displayed as the endoscope-like image has been explained in the embodiments described above. However, the present invention is effective to display information inherent to the MRI by displaying, for example, fat signals in an emphasized mode, in addition to the above. Further, the present invention is also effective to take an endoscope-like image of every body cavity other than a blood vessel.

The invention claimed is:

1. A method in a magnetic resonance (MR) imaging apparatus, said method comprising:

providing at least one peculiar index, which can be discriminated from other portions on art MR image, at the tip of a catheter;

previously inserting a metal guide wire for guiding the catheter into a body cavity of a patient into which the catheter is inserted;

executing, by said magnetic resonance imaging apparatus, an MR imaging sequence of a plurality of sliced images intersecting the guide wire while inserting the catheter into the body cavity along the guide wire;

receiving the nuclear magnetic resonance signals, which are generated from the patient when the sequence is executed, by using the guide wire as antenna means to receive said nuclear magnetic resonance signals;

reconstructing, by said magnetic resonance imaging apparatus, three-dimensional image data using the nuclear magnetic resonance signals;

determining the tip position and the insetting direction of the catheter by detecting the peculiar index provided at the tip of the catheter based on any one of the three-dimensional image data and image data imaged by an MR imaging method different from that of the three-dimensional image data;

setting the tip position and the inserting direction of the catheter as a view point and a line-of-sight direction, respectively;

acquiring, by said magnetic resonance imaging apparatus, three-dimensional image data at a plurality of sliced positions set forward of the tip of the catheter; and reconstructing, by said magnetic resonance imaging apparatus, a center projected image being observed from the view point by projecting the three-dimensional image data acquired at the sliced positions set forward of the tip of the catheter along a line-of-sight direction to a projection plane and displaying the center projected image on a display means.

2. A method in a magnetic resonance (MR) imaging apparatus, said method comprising:

providing at least one peculiar index, which can be discriminated from other portions on an MR image, at the tip of a catheter;

previously inserting it metal guide wire for guiding the catheter into a body cavity of a patient into which the catheter is inserted;

inserting the catheter into the body cavity along the guide wire;

executing, by said magnetic resonance imaging apparatus, an MR imaging sequence of a plurality of sliced images intersecting the guide wire;

reconstructing, by said magnetic resonance imaging apparatus, three-dimensional image data based upon the nuclear magnetic resonance signals, which are generated from the patient when the sequence is executed and are received by using the guide wire as antenna means to receive said nuclear magnetic resonance signals, and determining the tip position and the inserting direction of the catheter by detecting the peculiar index provided at the tip of the catheter based on the three-dimensional image data;

setting the tip position and the inserting direction of the catheter as a view point and a line-of-sight direction, respectively;

acquiring, by said magnetic resonance imaging apparatus, three-dimensional image data at a plurality of sliced positions set forward of the tip of the catheter; and reconstructing, by said magnetic resonance imaging apparatus, a center projected image being observed from the view point by projecting the three-dimensional image data acquired at the sliced positions set forward of the tip of the catheter along a line-of-sight direction to a projection plane and displaying the center projected image on a display means.

3. A method in a magnetic resonance (MR) imaging apparatus, said method comprising:

providing at least one peculiar index, which can be discriminated from other portions on an MR image, at the tip of a catheter;

previously inserting a metal guide wire for guiding the catheter into a body cavity of a patient into which the catheter is inserted;

executing, by said magnetic resonance imaging apparatus, an MR imaging sequence of a plurality of sliced images intersecting the guide wire, reconstructing three-dimensional image data based upon the nuclear magnetic resonance signals, which are generated from the patient when the sequence is executed, received by using the guide wire as antenna means to receive said nuclear magnetic resonance signals, and storing the three-dimensional image data;

inserting the catheter into the body cavity along the guide wire;

executing, by said magnetic resonance imaging apparatus, a measuring sequence to the tip of the catheter in the three-axis directions thereof to acquire nuclear magnetic resonance signals, receiving the nuclear magnetic resonance signals, which are generated from the patient when the sequence is executed, by a receiving coil disposed outside of the patient, and determining the tip position and the inserting direction of the catheter by detecting the peculiar index using the thus received nuclear magnetic resonance signals;

setting the tip position and the inserting direction of the catheter as a view point and a line-of-sight direction, respectively;

acquiring, by said magnetic resonance imaging apparatus, three-dimensional image data at a plurality of sliced positions set forward of the tip of the catheter; and reconstructing, by said magnetic resonance imaging apparatus, a center projected image being observed from the view point by projecting the three-dimensional image data acquired at the sliced positions set forward of the tip of the catheter along a line-of-sight direction to a projection plane and displaying the center projected image on a display means.

4. The method according to claim 3, characterized in that the MR imaging sequence of the plurality of sliced images is executed once each time processing for rearranging the center projected image is executed a plurality of times.

5. A method in a magnetic resonance (MR) imaging apparatus, said method comprising:

a preparation step of providing at least one peculiar index, which can be discriminated from other portions on an MR image, at the tip of a catheter;

a first step of previously inserting a metal guide wire for guiding the catheter into a body cavity of a patient into which the catheter is inserted;

a second step of inserting the catheter into the body cavity along the guide wire;

a third step of executing, by said magnetic resonance imaging apparatus, an MR measuring sequence to the tip of the catheter in each of the three-axis directions thereof, receiving the nuclear magnetic resonance signals, which are generated from the patient when the sequence is executed, by using a receiving coil disposed outside of the patient as antenna means to receive said nuclear magnetic resonance signals, and determining the tip position and the inserting direction of the catheter by detecting the peculiar index provided at the tip of the catheter;

a fourth step of executing an MR imaging sequence of a plurality of sliced images intersecting the guide wire; and a fifth step of reconstructing, by said magnetic resonance imagine apparatus, three-dimensional image data based upon the nuclear magnetic resonance signals, which are generated from the patient when the sequence is executed and are received by the guide wire, setting the tip position and the inserting direction of the catheter as a view point and a line-of-sight direction, respectively, acquiring, by said magnetic resonance imaging apparatus, three-dimensional image data at a plurality of sliced positions set forward of the tip of the catheter and reconstructing, by said magnetic resonance imaging apparatus, a center projected image being observed from the view point by projecting the three-dimensional image data acquired at the sliced positions set forward of the tip of the catheter along a line-of-sight direction, and displaying the center projected image on a display means.

6. The method according to claim 5, characterized in that the sliced positions imaged at the fourth step are set forward of the tip of the catheter.

7. The method according to any one of claims 1 to 6, characterized in that the peculiar index is a ring-shaped marker provided at the tip of the catheter coaxially with the catheter.

8. The method according to claim 7, characterized in that at least two markers are provided at the tip of the catheter in such a manner that the positions thereof are displaced in the axial direction of the catheter.

9. A magnetic resonance imaging apparatus comprising:
magnetic field generation means for generating the respective magnetic fields of a static magnetic field, a gradient magnetic field, and a high frequency magnetic field, receiving means for receiving the nuclear magnetic resonance signals generated from the patient, image reconstruction means for reconstructing an image based on the thus received nuclear magnetic resonance signals, display means for displaying the image, and control means for controlling the magnetic field generation means and the receiving means, applying the high frequency magnetic field and the gradient magnetic field to the patient placed in the static magnetic field, and causing an imaging sequence for receiving the nuclear magnetic resonance signals to be executed, characterized in that:

the receiving means comprises a receiving coil disposed outside of the patient and a guide wire inserted into a body cavity of the patient;

a catheter guided by the guide wire has at least one peculiar index, which can be discriminated from other portions on an MR image, at the tip thereof; and the control means has:

a function for causing the image reconstruction means to reconstruct three-dimensional image data using the nuclear magnetic resonance signals received by the guide wire and causing the three-dimensional image data to be stored in a memory means;

a function for causing a measuring sequence to be executed to measure NMR signals of the tip of the catheter in the three-axis directions thereof;

a function for controlling the image reconstruction means and determining the tip position and the inserting direction of the catheter by detecting the peculiar index using the nuclear magnetic resonance signals received by the receiving coil when the measuring sequence is executed;

a function for controlling the image reconstruction means and causing the image reconstruction means to set the tip position and the inserting direction of the catheter as a view point and a line-of-sight direction, respectively, acquire three-dimensional image data at a plurality of sliced positions set forward of the tip of the catheter, and reconstruct a center projected image being observed from the view point by projecting the three-dimensional image data acquired at the sliced positions set forward of the tip of the catheter along a line-of-sight direction to a projection plane; and a function for causing the thus reconstructed center projected image to be displayed on the display means.

10. A magnetic resonance imaging apparatus comprising:
magnetic field generation means for generating the respective magnetic fields of a static magnetic field, a gradient magnetic field, and a high frequency magnetic field, receiving means for receiving the nuclear magnetic resonance signals generated from the patient, image reconstruction means for reconstructing an image based on the thus received nuclear magnetic resonance signals, display means for displaying the image, and control means for controlling the magnetic field generation means and the receiving means, applying the high frequency magnetic field and the gradient magnetic field to the patient placed in the static magnetic field, and causing an imaging sequence for receiving the nuclear magnetic resonance signals to be executed, characterized in that:

the receiving means comprises a receiving coil disposed outside of the patient and a guide wire inserted into a body cavity of the patient;

the catheter guided by the guide wire has at least one peculiar index, which can be discriminated from other portions on an MR image, at the tip thereof; and the control means has:

a function for causing a measuring sequence to he executed to acquire the nuclear magnetic resonance signals of the tip of the catheter in the three-axis directions thereof;

a function for controlling the image reconstruction means and determining the tip position and the inserting direction of the catheter by detecting the peculiar index using the nuclear magnetic resonance signals received by the receiving coil when the measuring sequence is executed;

a function for causing an imaging sequence to be executed to image a plurality of sliced planes intersecting the guide wire;

a function for controlling the image reconstruction means and causing the image reconstruction means to reconstruct the three-dimensional image data using the nuclear magnetic resonance signals received by the guide wire;

a function for controlling the image reconstruction means and causing the image reconstruction means to set the tip position and the inserting direction of the catheter as a view point and a line-of-sight direction, respectively, acquire three-dimensional image data at a plurality of sliced positions set forward of the tip of the catheter, and reconstruct a center projected image being observed from the view point by projecting the three-dimensional image data acquired at the sliced positions set forward of the tip of the catheter along a line-of-sight direction to a projection plane; and a function for causing the thus reconstructed center projected image to be displayed on the display means.

11. A magnetic resonance imaging apparatus comprising:
magnetic field generation means for generating the respective magnetic fields of a static magnetic field, a gradient magnetic field, and a high frequency magnetic field that are applied to a patient, receiving means for receiving the nuclear magnetic resonance signals generated from the patient, image reconstruction means for reconstructing the three-dimensional image data of the patient using the thus received nuclear magnetic resonance signals, display means for displaying a reconstructed image, and control means for controlling the magnetic field generation means, the receiving means, and the image reconstruction means, characterized in that:

at least one peculiar index, which can be discriminated from other portions on an MR image, is provided at the tip of a catheter inserted into a body cavity of the patient as well as a metal guide wire for guiding the catheter is used as the receiving means; and the image reconstruction means reconstructs three-dimensional image data using the nuclear magnetic resonance signals received by the guide wire, detects the peculiar index using the reconstructed three-dimensional image data, determines the tip position and the inserting direction of the catheter bused on the peculiar index, sets the tip position and the inserting direction of the catheter as a view point and a line-of-sight direction, respectively, acquires three-dimensional image data at a plurality of sliced positions set forward of the tip of the catheter, and reconstructs a center projected image being observed from the view point by projecting the three-dimensional image data acquired at the sliced positions set forward of the tip of the catheter along a line-of-sight direction to a projection plane, and displays the center projected image on the display means.

12. A magnetic resonance imaging apparatus according to any of claims 11 to 10, characterized in that the image of the wall surface in a body cavity forward of the inserting direction of the catheter is displayed on the display means by being varied according to an inserted position of the catheter.

13. A magnetic resonance imaging apparatus according to any one of claims 11 to 10, characterized in that the peculiar index is a ring-shaped marker provided at the tip of the catheter coaxially with the catheter.

14. A magnetic resonance imaging apparatus according to claim 13, characterized in that at least two markers are provided at the tip of the catheter in such a manner that the positions thereof are displaced in the axial direction of the catheter.

15. A magnetic resonance imaging apparatus according to any one of claims 11 to 10, characterized in that the control means repeats a first step of executing an imaging sequence for acquiring the three-dimensional image data, a second step of determining the tip position and the inserting direction of the catheter, and a third step of rearranging and displaying the center projected image.

16. A magnetic resonance imaging apparatus according to claim 15, characterized in that the control means executes the first step once each time the first to third steps are repeated a plurality of times.

17. A method in a magnetic resonance (MR) imaging apparatus, said method comprising:

a first step of inserting a metal guide wire into a body cavity of a patient;

a second step of inserting a catheter, which provides an least one peculiar index at a tip thereof, into a body cavity along the guide wire;

a third step of executing, by said magnetic resonance imaging apparatus, an MR imaging sequence of a plurality of sliced images intersecting the guide wire and receiving nuclear magnetic resonance signals by using the guide wire as antenna means to receive said nuclear magnetic resonance signals;

a fourth step of reconstructing, by said magnetic resonance imaging apparatus, three-dimensional image data based upon the nuclear magnetic resonance signals;

a fifth step of determining the tip position and the inserting direction of the catheter based on the peculiar index provided at the tip of the catheter; and a sixth step of setting the tip position and the inserting direction of the catheter as a view point and a line-of-sight direction, respectively, acquiring, by said magnetic resonance imaging apparatus, three-dimensional image data at a plurality of sliced positions set forward of the tip of the catheter, reconstructing, by said magnetic resonance imaging apparatus, a center projected image being observed from the view point by projecting the three-dimensional image data acquired at the sliced positions set forward of the tip of the catheter along a line-of-sight direction to a projection plane, and displaying the center projected image on a display means.

18. The method according to claim 17, wherein
said fifth step determines the tip position of the catheter by detecting the peculiar index based on the three-dimensional image data.

19. The method according to claim 17, wherein
said fifth step determines an inserting direction of the catheter by detecting the peculiar index based on the three-dimensional image data; and said sixth step rearranges the center projected image using the three-dimensional image data and the tip position and an inserting direction of the catheter as the view point and a line-of-sight direction.

20. A method in a magnetic resonance (MR) imaging apparatus, said method comprising:

executing, by said magnetic resonance imaging apparatus, an MR imaging sequence of a plurality of sliced images intersecting a guide wire while inserting the catheter into a body cavity along the guide wire;

receiving nuclear magnetic resonance signals, which are generated from a patient when the sequence is executed, by using the guide wire as antenna means to receive said nuclear magnetic resonance signals;

reconstructing, by said magnetic resonance imaging apparatus, three-dimensional image data using the nuclear magnetic resonance signals;

determining the tip position and the inserting direction of the catheter by detecting at least one peculiar index provided at the tip of the catheter based on any one of the three-dimensional image data and image data imaged by an MR imaging method different from that of the three-dimensional image data;

setting the tip position and the inserting direction of the catheter as a view point and a line-of-sight direction respectively;

acquiring, by said magnetic resonance imaging apparatus, three-dimensional image data at a plurality of sliced positions set forward of the tip of the catheter;

reconstructing, by said magnetic resonance imaging apparatus a center projected image being observed from the view point by projecting the three-dimensional image data acquired at the sliced positions set forward of the tip of the catheter along the line-of-sight direction to a projection plane; and displaying the center projected image on a display means.

21. The method according to claim 20, further comprising:
inserting the metal guide wire, previously executing the MR imaging sequence, for guiding the catheter into the body cavity of the patient into which the catheter is inserted.

22. The method according to claim 20, further comprising:
determining an inserting direction of the catheter by detecting the peculiar index based on any one of the three-dimensional image data and image data imaged by an MR imaging method different from that of the three-dimensional image data;

rearranging the center projected image using the three-dimensional image data by taking the tip position and the inserting direction of the catheter as the view point and a line-of sight direction.

23. A method in a magnetic resonance (MR) imaging apparatus, said method comprising:
a first step of previously inserting a metal guide wire far guiding the catheter into a body cavity of a patient into which the catheter is inserted;
a second step of executing, by said magnetic resonance imaging apparatus, an MR imaging sequence of a plurality of sliced images intersecting the guide wire, reconstructing by said magnetic resonance imaging apparatus, three-dimensional image data based upon the nuclear magnetic resonance signals, which are generated from the patient when the sequence is executed, received by the guide wire, and storing the three-dimensional image data;
a third step of inserting the catheter into the body cavity along the guide wire;
a fourth step of executing a measuring sequence to the tip of the catheter in the three-axis directions thereof to acquire nuclear magnetic resonance signals, receiving the nuclear magnetic resonance signals, which are generated from the patient when the sequence is executed, by using a receiving coil disposed outside of the patient as antenna means to receive said nuclear magnetic resonance signals, and determining the tip position and an inserting direction of the catheter by detecting a peculiar index provided at the tip of the catheter, using the thus received nuclear magnetic resonance signals; and
a fifth step of setting the tip position and the inserting direction of the catheter as a view point and a line-of-sight direction, respectively, acquiring, by said, magnetic resonance imaging apparatus, three-dimensional image data at a plurality of sliced positions set forward of the tip of the catheter, reconstructing, by said magnetic resonance imaging apparatus, a center projected image being observed from the view point by projecting the three-dimensional image data acquired at the sliced positions set forward of the tip of the catheter along a line-of-sight direction to a projection plane, and displaying the center projected image on a display means.

24. The method according to claim 23, wherein
the fifth step reconstructs the center projected image using the three-dimensional image data by taking the tip position and the inserting direction of the catheter as the view point and a line-of-sight direction.

25. A method in a magnetic resonance (MR) imaging apparatus, said method comprising:
a first step of previously inserting a metal guide wire for guiding a catheter into a body cavity of a patient into which the catheter is inserted;
a second step of inserting the catheter provided at least one peculiar index at a top thereof into the body cavity along the guide wire;
a third step of executing, by said magnetic resonance imaging apparatus, an MR measuring sequence to a tip of the catheter in each of the three-axis directions thereof, receiving nuclear magnetic resonance signals, which are generated from the patient when the sequence is executed, by using a receiving coil disposed outside of the patient as antenna means to receive said nuclear magnetic resonance signals, and determining the tip position of the catheter by detecting the peculiar index provided at the tip of the catheter;
a fourth step of executing, by said magnetic resonance imaging apparatus, an MR imaging sequence of a plurality of sliced images intersecting the guide wire; and
a fifth step of reconstructing, by said magnetic resonance imagine apparatus, three-dimensional image data based upon the nuclear magnetic resonance signals, which are generated from the patient when the sequence is executed and are received by the guide wire, setting the tip position and the inserting direction of the catheter as a view point and a line-of-sight direction, respectively, acquiring three-dimensional image data at a plurality of sliced positions set forward of the tip of the catheter, reconstructing, by said magnetic resonance imaging apparatus, a center projected image being observed from the view point by projecting the three-dimensional image data acquired at the sliced positions set forward of the tip of the catheter along a line-of-sight direction to a projection plane, and displaying the center projected image on a display news.

26. The method according to claim 25, wherein
the fifth step reconstructs the center projected image rearranging the center projected image using the three-dimensional image data by taking the tip position and the inserting direction of the catheter as the view point and a line-of-sight direction.

27. A magnetic resonance imaging apparatus comprising:
magnetic field generation means for generating the respective magnetic fields of a static magnetic field, a gradient magnetic filed, and a high frequency magnetic field that are applied to a patient;
receiving means for receiving nuclear magnetic resonance signals generated from the patient, image reconstruction means for reconstructing three-dimensional image data of the patient using the thus received the nuclear magnetic resonance signals,
display means for displaying a reconstructed image, and
a control means for controlling the magnetic field generation means, the receiving means, and the image reconstruction means, characterized in that:
at least one peculiar index, which can be discriminated from other portions on an MR image, is provided at the tip of a catheter inserted into a body cavity of the patient as well as a metal guide wire for guiding the catheter is used as the receiving means; and
the image reconstruction means reconstructs the three-dimensional image data using the nuclear magnetic resonance signals received by the guide wire, determines the tip position and the inserting direction of the catheter based on the peculiar index, sets the tip position and the inserting direction of the catheter as a view point and a line-of-sight direction, respectively, acquiring three-dimensional image data at a plurality of sliced positions set forward of the tip of the catheter and reconstructs a center projected image being observed from the view point by projecting the three-dimensional image data acquired at the sliced positions set forward of the tip of the catheter along a line-of-sight direction to a projection plane, and displays the center projected image on the display means.

28. A magnetic resonance imaging apparatus according to claim 27 wherein:
the image reconstruction means determines the tip position of the catheter using an image of the peculiar index of the three-dimensional image data.

29. A magnetic resonance imaging apparatus according to claim 27 wherein:
the image reconstruction means determines an inserting direction of the catheter using the image of the peculiar index of the three-dimensional image data, and reconstructs a center projected image using the three-dimensional image data by taking the tip position and the inserting direction of the catheter as a view point and a line-of-sight direction.

30. A magnetic resonance imaging apparatus comprising:
magnetic field generation means for generating the respective magnetic fields of a static magnetic field, a gradient magnetic field, and a high frequency magnetic field, receiving means for receiving the nuclear magnetic resonance signals generated from the patient, image reconstruction means for reconstructing an image based on the thus received nuclear magnetic resonance signals, display means for displaying the image, and control means for controlling the magnetic field generation means and the receiving means, applying the high frequency magnetic field and the gradient magnetic field to the patient placed in the static magnetic field, and causing an imaging sequence for receiving the nuclear magnetic resonance signals to be executed, characterized in that:
the receiving means comprises a receiving coil disposed outside of the patient and a guide wire inserted into a body cavity of the patient;
a catheter guided by the guide wire has at least one peculiar index, which can be discriminated from other portions on an MR image, at the tip thereof; and
the control means has:
a function for causing the image reconstruction means to reconstruct three-dimensional image data using the nuclear magnetic resonance signals received by the guide wire and causing the three-dimensional image data to be stored in a memory means;
a function for causing a measuring sequence to be executed to measure NMR signal of the tip of the catheter in the three-axis directions thereof;
a function for controlling the image reconstruction means and determining the tip position of the catheter by detecting the peculiar index using the nuclear magnetic resonance signals received by the receiving coil when the measuring sequence is executed;
a function for controlling the image reconstruction means and causing the image reconstruction means to set the tip position and the inserting direction of the catheter as a view point and a line-of-sight direction, respectively, acquiring three-dimensional image data at a plurality of sliced positions set forward of the tip of the catheter and reconstruct a center projected image being observed from the view point by projecting the three-dimensional image data acquired at the sliced positions set forward of the tip of the catheter along a line-of-sight direction to a projection plane; and
a function for causing the thus reconstructed center projected image to be displayed on the display means.

31. A magnetic resonance imaging apparatus according to claim 30, wherein
the image reconstruction means determines the tip position of the catheter using an image of the peculiar index of the three-dimensional image data.

32. A magnetic resonance imaging apparatus according to claim 30, wherein
the image reconstruction means determines an inserting direction of the catheter using the image of the peculiar index of the three-dimensional image data, and reconstructs a center projected image using the three-dimensional image data by taking the tip position and the inserting direction of the catheter us a view point and a line-of-sight direction.

33. A magnetic resonance imaging apparatus comprising:
magnetic field generation means for generating the respective magnetic fields of a static magnetic field, a gradient magnetic field, and a high frequency magnetic field, receiving means for receiving the nuclear magnetic resonance signals generated from the patient, image reconstruction means for reconstructing an image based on the thus received nuclear magnetic resonance signals, display means for displaying the image, and control means for controlling the magnetic field generation means and the receiving means, applying the high frequency magnetic field and the gradient magnetic field to the patient placed in the static magnetic field, and causing an imaging sequence for receiving the nuclear magnetic resonance signals to be executed, characterized in that:
the receiving means comprises a receiving coil disposed outside of the patient and a guide wire inserted into a body cavity of the patient;
a catheter guided by the guide wire has at least one peculiar index, which can be discriminated from other portions on an MR image, at the tip thereof; and
the control means has:
a function for causing a measuring sequence to be executed to acquire the nuclear magnetic resonance signals of the tip of the catheter in three-axis directions thereof;
a function for controlling the image reconstruction means and determining the tip position and the inserting direction of the catheter by detecting the peculiar index using the nuclear magnetic resonance signals received by the receiving coil when the measuring sequence is executed;
a function for causing an imaging sequence to be executed to image a plurality of sliced planes intersecting the guide wire;
a function for controlling the image reconstruction means and causing the image reconstruction means to reconstruct the three-dimensional image data using the nuclear magnetic resonance signals received by the guide wire:
a function for controlling the image reconstruction means and causing the image reconstruction means to set the tip position and the inserting direction of the catheter as a view point and a line-of-sight direction, respectively, acquiring three-dimensional image data at a plurality of sliced positions set forward of the tip of the catheter and reconstruct a center projected image being observed from the view point by projecting the three-dimensional image data acquired at the sliced positions set forward of the tip of the catheter along a line-of-sight direction to a projection plane; and
a function for causing the thus reconstructed center projected image to be displayed on the display means.

34. A magnetic resonance imaging apparatus according to claim 33, wherein
the image reconstruction means determines the tip position of the catheter using an image of the peculiar index of the three-dimensional image data.

35. A magnetic resonance imaging apparatus according to claim 33, wherein
the image reconstruction means determines an inserting direction of the catheter using the image of the peculiar index of the three-dimensional image data, and reconstructs the center projected image using the three-dimensional image data by taking the tip position and the inserting direction of the catheter as a view point and a line-of sight direction.

* * * * *